(12) United States Patent
Sanders et al.

(10) Patent No.: US 12,305,241 B2
(45) Date of Patent: *May 20, 2025

(54) EML4-ALK TRANSLOCATIONS IN LUNG CANCER

(71) Applicant: Quest Diagnostics Investments LLC, Secaucus, NJ (US)

(72) Inventors: Heather R. Sanders, Winchester, CA (US); Maher Albitar, Coto De Caza, CA (US); Aurelia Meloni-Ehrig, Gainesville, VA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/141,862

(22) Filed: May 1, 2023

(65) Prior Publication Data
US 2023/0416835 A1    Dec. 28, 2023

Related U.S. Application Data

(60) Continuation of application No. 16/594,718, filed on Oct. 7, 2019, now Pat. No. 11,639,529, which is a continuation of application No. 15/952,424, filed on Apr. 13, 2018, now Pat. No. 10,435,758, which is a division of application No. 14/928,347, filed on Oct. 30, 2015, now Pat. No. 9,957,573, which is a continuation of application No. 13/518,232, filed as application No. PCT/US2010/060858 on Dec. 16, 2010, now Pat. No. 9,175,350.

(60) Provisional application No. 61/301,551, filed on Feb. 4, 2010, provisional application No. 61/289,234, filed on Dec. 22, 2009.

(51) Int. Cl.
*C12Q 1/6886* (2018.01)

(52) U.S. Cl.
CPC ..... *C12Q 1/6886* (2013.01); *C12Q 2537/143* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,468,613 | A | 11/1995 | Erlich et al. | |
| 6,399,364 | B1 | 6/2002 | Reeve et al. | |
| 9,175,350 | B2 * | 11/2015 | Sanders | C12Q 1/6886 |
| 10,435,758 | B2 * | 10/2019 | Sanders | C12Q 1/6886 |
| 11,639,529 | B2 * | 5/2023 | Sanders | C12Q 1/6886 |
| | | | | 435/6.12 |
| 2002/0182622 | A1 | 12/2002 | Nakamura et al. | |
| 2006/0281108 | A1 | 12/2006 | Monforte et al. | |
| 2008/0090776 | A1 | 4/2008 | Mano et al. | |

FOREIGN PATENT DOCUMENTS

EP    1914240 B1 * 12/2009 ........... A61K 31/506

OTHER PUBLICATIONS

Choi et al., "Transforming Gene in Non-Small Cell Lung Cancer," Cancer Research, vol. 68, pp. 4971-4976, 2008.
Fukuyoshi et al., "EML4-ALK fusion transcript is not found in gastrointestinal and breast cancers," British Journal of Cancer, vol. 98, pp. 1536-1539, 2008.
Horn, L. et al. "EML4-ALK: Honing in on a New Target in Non-Small-Cell Lung Cancer". Journal of Clinical Oncology, vol. 27 No. 26, Sep. 10, 2009, pp. 4232-4235.
Inamura et al., "EML4-ALK Fusion is Linked to Histological Characteristics in a Subset of Lung Cancers," Journal of Thoracic Oncology, vol. 3, No. 1, pp. 13-17, Jan. 2008.
International Search Report mailed Jul. 12, 2011 in Int'l Appl. PCT/US2010/060858 (5 pages.).
Kleparnik et al., "DNA Diagnostics by Capillary Electrophoresis," Chem. Rev. 2007, 107:5279-5317.
Merriam-Webster, "Detect," Free Merriam-Webster Dictionary, http://www.merriam-webster.com/dictionary/detect, accessed May 20, 2014.
Mitsuhashi et al., "Technical Report: Part 2. Basic Requirements for Designing Optimal PCR Primers," Journal of Clinical Laboratory Analysis, 10:285-293, 1996.
Notice of Allowance dated Dec. 22, 2022 in U.S. Appl. No. 16/594,718.
Notice of Allowance dated May 24, 2019 in U.S. Appl. No. 15/952,424.
Notice of Allowance issued in U.S. Appl. No. 13/518,232 on Jun. 22, 2015.
Notice of Allowance issued in U.S. Appl. No. 14/928,347 on Dec. 22, 2017.
Office Action dated Jan. 28, 2019 in U.S. Appl. No. 15/952,424.
Office Action dated Dec. 2, 2021 in U.S. Appl. No. 16/594,718.
Office Action dated Apr. 18, 2022 in U.S. Appl. No. 16/594,718.
Office Action dated Apr. 26, 2021 in U.S. Appl. No. 16/594,718.
Office Action dated Aug. 28, 2018 in U.S. Appl. No. 15/952,424.
Office Action dated Sep. 14, 2022 in U.S. Appl. No. 16/594,718.
Office Action issued in U.S. Appl. No. 13/518,232 on Feb. 6, 2015.
Office Action issued in U.S. Appl. No. 13/518,232 on Mar. 28, 2014.
Office Action issued in U.S. Appl. No. 13/518,232 on Sep. 11, 2014.
Office Action issued in U.S. Appl. No. 14/928,347 on Jun. 7, 2017.
Office Action issued in U.S. Appl. No. 14/928,347 on Oct. 6, 2017.
Sanders, H. et al. "Somatic mutations of signaling genes in non-small-cell lung cancer". Cancer Genetics and Cytogenetics, vol. 203, 2010, pp. 7-15.

(Continued)

*Primary Examiner* — Carla J Myers
(74) *Attorney, Agent, or Firm* — Foley & Lardner LLP

(57) ABSTRACT

The present disclosure relates to methods for the diagnosis and evaluation of neoplastic disorders, particularly non-small cell lung cancer. Assays are described in which patient test samples are analyzed for the presence of one or more specific EML4-ALK fusion genes associated with neoplastic disorders.

8 Claims, 2 Drawing Sheets

Specification includes a Sequence Listing.

(56) References Cited

OTHER PUBLICATIONS

Sigma Life Science, "qPCR Technical Guide," 2008, p. 1-43, available via URL: <users.stlcc.edu/Departments/fvbio/Thermal_Cycler_sigma%20qpcr_technical_guide.pdf> (Year: 2008).

Takahashi, T. et al. "Clinicopathologic Features of Non-Small-Cell Lung Cancer with EML4-ALK Fusion Gene". Annals of Surgical Oncology, vol. 17, 2010, pp. 889-897.

Takeuchi et al., "Multiplex Reverse Transcription-PCR Screening for EML4-ALK Fusion Transcripts," Clinical Cancer Research, 2008, 14(2):6618-6624.

The Free Dictionary, "Determining," Free Online Dictionary, http://www.thefreedictionary.com/determining, accessed Mar. 4, 2014.

* cited by examiner

EML4-ALK TRANSLOCATIONS IN LUNG CANCER

CROSS-REFERENCE TO RELATED APPLICATIONS

This application is a continuation of U.S. patent application Ser. No. 16/594,718, filed Oct. 7, 2019, which is a continuation of U.S. patent application Ser. No. 15/952,424, filed Apr. 13, 2018, which is a divisional of U.S. patent application Ser. No. 14/928,347, filed Oct. 30, 2015, now U.S. Pat. No. 9,957,573, which is a continuation of U.S. patent application Ser. No. 13/518,232, filed Aug. 31, 2012, now U.S. Pat. No. 9,175,350, which is a U.S. National Stage of PCT/US2010/060858, filed Dec. 16, 2010, which claims benefit of U.S. Provisional Applications 61/289,234, filed on Dec. 22, 2009 and 61/301,551, filed Feb. 4, 2010, incorporated by reference herein in their entirety.

The instant application contains a Sequence Listing which has been submitted in XML format via Patent Center and is hereby incorporated by reference in its entirety. Said XML copy, created on May 19, 2023, is named 034827-1925_SL.xml and is 39,005 bytes.

FIELD OF THE INVENTION

The present invention relates generally to the field of medical diagnostics. In particular, the present technology relates to methods of detecting genetic mutations associated with cancer.

BACKGROUND OF THE INVENTION

The following description is provided to assist the understanding of the reader. None of the information provided or references cited is admitted to be prior art to the present invention.

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases. Among these cancers are solid tumors, like non-small cell lung cancer (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. NSCLC, which comprises three distinct subtypes, is often only detected after it has metastasized, and thus the mortality rate is 75% within two years of diagnosis.

It is known that gene deletions and/or translocations resulting in kinase fusion proteins with aberrant signaling activity can directly lead to certain cancers. For example, it has been demonstrated that the BCR-ABL oncoprotein, a tyrosine kinase fusion protein, is a causative agent in human chronic myelogenous leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia and NSCLC cases.

EML4-ALK is a fusion-type protein tyrosine kinase that is generated in human non-small-cell lung cancer (NSCLC) and other cancers as a result of a recurrent chromosome inversion, inv (2)(p21p23). EML4 (echinoderm microtubule-associated protein like protein 4) is a cytoplasmic protein with a molecular weight of 120,000, which is highly expressed in the M phase of the cell cycle. The human EML4 gene encodes a polypeptide with 981 amino acids and has 23 exons. The EML4 protein has a basic region at the amino terminus, as with other members of the EML family, and further has carboxyl-terminal WD domains. The function of EML4 in cells is not known. However, according to a recent report, EML4 may participate in microtubule formation.

ALK (Anaplastic Lymphoma Kinaseis receptor tyrosine kinase) is a protein that has a transmembrane domain in the central part, a carboxyl-terminal tyrosine kinase region, and an amino-terminal extracellular domain. The ALK gene has 30 exons and encodes a polypeptide with 1,620 amino acids. The ALK gene has been reported to participate in the development or functioning of the nervous system. Full-length ALK expression has been reported in some cancer cells of ectodermal origin, such as neuroblastoma, glioblastoma, breast cancer, and melanoma.

SUMMARY OF THE INVENTION

In one aspect, the present invention provides a method for diagnosing a neoplastic disorder or susceptibility to a neoplastic disorder comprising detecting the presence of a EML4-ALK gene fusion in a sample from a subject, wherein the EML4-ALK gene fusion is a fusion between exon 17 or intron 17 of EML4 and intron 19 of ALK, and diagnosing the subject as having or being susceptible to a neoplastic disorder when the gene fusion is present.

In another aspect, the invention provides a method of determining the EML4-ALK gene fusion status of a human by: (a) determining the presence or absence of the E17; ins30A20 or E17ins30; ins65A20 gene fusion in both alleles of the of the EML4-ALK fusion gene of the human in a nucleic acid sample obtained from the human, and (b) identifying the human (i) as being homozygous for E17; ins30A20 or E17ins30; ins65A20 gene fusion in the EML4-ALK fusion gene when one of the gene fusions is present in both alleles of the EML4-ALK fusion gene, or (ii) as being heterozygous for the E17; ins30A20 or E17ins30; ins65A20 gene fusion in the EML4-ALK fusion gene when one of the gene fusions is present in one of the alleles of the EML4-ALK fusion gene, or (iii) as having no alteration in the EML4-ALK fusion gene caused by the E17; ins30A20 or E17ins30; ins65A20 gene fusion when each of the gene fusions is absent from both alleles of the EML4-ALK fusion gene.

In some embodiments, the neoplastic disorder is non small cell lung cancer.

In some embodiments, the EML4-ALK gene fusion is E17; ins30A20 or E17ins30; ins65A20. An EML4-ALK gene fusion may be detected by amplifying SEQ ID NO: 1, SEQ ID NO: 2, or a diagnostic fragment thereof. In one embodiment, the method includes detecting one or more additional EML4-ALK gene fusions in a sample from the subject. For instance, the one or more additional EML4-ALK gene fusions may be selected from the group consisting of: variant 1, variant 2, variant 3a, variant 3b, variant 4, variant 5a, variant 5b, variant 6, and variant 7.

Suitable samples for assessment of EML4-ALK fusions include, for example, plasma, serum, and biopsy tissue (e.g., a lung biopsy sample).

The EML4-ALK fusion may be detected by assessing sample nucleic acid by PCR, RT-PCR, and/or nucleic acid hybridization. In one embodiment, the sample is amplified by reverse transcriptase polymerase chain reaction (RT-PCR). In one embodiment, the amplifying employs a detectably labeled primer. In one embodiment, the detecting is accomplished with electrophoresis. In one embodiment, the detecting is accomplished using a real-time PCR-based detection system, such as TaqMan®.

The present invention also provides a method for diagnosing a neoplastic disorder or susceptibility to a neoplastic disorder by detecting the presence or absence of an EML4-ALK fusion protein in a sample from a subject, wherein the EML4-ALK fusion protein is a fusion between exon 17 or intron 17 of EML4 and intron 19 of ALK, and diagnosing the subject has having or being susceptible to a neoplastic disorder when the fusion protein is present. In one embodiment, the fusion protein contains the sequence of SEQ ID NO: 29 or 30.

The invention also provides kits for detecting a EML4-ALK fusion mutations which include one or more oligonucleotides (e.g., a primer) for amplifying a fragment of a nucleic acid sample which contains the E17; ins30A20 or E17ins30; ins65A20 mutation, if present. In one embodiment, at least one of the primers contains the sequence of SEQ ID NOs: 19 and 25, or complements thereof. Optionally, the kit further contains one or more mutation-specific oligonucleotide probes. In a related aspect, the invention provides a kit containing at least one oligonucleotide having the sequence of SEQ ID NOs: 19 or 25-28, or complements thereof.

In another aspect, the invention provides an isolated polynucleotide substantially identical to SEQ ID NO: 1 or SEQ ID NO: 2 or complements thereof. Other useful a substantially purified polynucleotides include those having the sequence of any of SEQ ID NOs: 3-25 or complements thereof.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a nucleic acid" includes a combination of two or more nucleic acids, and the like.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, CA 1990, pp. 13-20; Wharam et al., *Nucleic Acids Res.,* 2001, 29(11):E54-E54; Hafner et al., *Biotechniques* 2001, 30(4):852-6, 858, 860; Zhong et al., *Biotechniques,* 2001, 30(4):852-6, 858, 860.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein the terms "diagnose" or "diagnosis" or "diagnosing" refer to distinguishing or identifying a disease, syndrome or condition or identifying a person having a particular disease, syndrome or condition. In illustrative embodiments of the invention, assays are used to diagnose a neoplastic disorder, such as NSCLC, in a subject based on an analysis of a sample.

As used herein, the term "EML4-ALK gene fusion" refers to an aberrant gene rearrangement between the EML4 gene and the ALK gene on chromosome 2. The term EML4-ALK fusion also refers to the polypeptide formed from an inversion on human chromosome 2 in which the EML4 gene is fused to the ALK gene and that sequence is translated to form an aberrant protein. In exemplary embodiments, the EML4-ALK gene fusion is the EML4-ALK protein variant 8a or 8b, or encoding nucleic acids.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual,* Second Edition, Cold Spring Harbor Press, Plainview, N.Y.; Ausubel, F. M. et al. 1994, *Current Protocols in Molecular Biology*. John Wiley & Sons, Secaucus, N.J.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, a "fragment" means a linear segment of a target polynucleotide that is at least about 15, 20, 25, 30, 35, 40, 45, 50, 75, 100, 200, 300, 400, 500, 1000 contiguous nucleotides or more in length.

As used herein, the term "neoplastic disorder" refers to cancers of any kind and origin and precursor stages thereof.

Accordingly, the term "neoplastic disorder" includes the subject matter identified by the terms "neoplasia", "neoplasm", "cancer", "precancer" or "tumor". Neoplastic disorders to which the methods of the present invention may be applied include but are not limited to, neoplastic lesions of the respiratory tract, such as non-small cell lung cancer.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe.

An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human. In an exemplary embodiment, the sample is a biopsy sample.

"Target nucleic acid" as used herein refers to segments of a chromosome, a complete gene with or without intergenic sequence, segments or portions a gene with or without intergenic sequence, or sequence of nucleic acids to which probes or primers are designed. Target nucleic acids may include wild type sequences, nucleic acid sequences containing mutations, deletions or duplications, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein, target nucleic acid may be native DNA or a PCR-amplified product. In one embodiment, the target nucleic acid is a fragment of a chromosomal inversion involving a fusion of the EML4-ALK genes.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein the term "substantially identical" refers to a polypeptide or nucleic acid exhibiting at least 50%, 75%, 85%, 90%, 95%, or even 99% identity to a reference amino acid or nucleic acid sequence over the region of comparison. For polypeptides, the length of comparison sequences will generally be at least 20, 30, 40, or 50 amino acids or more, or the full length of the polypeptide. For nucleic acids, the length of comparison sequences will generally be at least 10, 15, 20, 25, 30, 40, 50, 75, or 100 nucleotides or more, or the full length of the nucleic acid.

As used herein, the term "patient" refers to a subject who receives medical care, attention or treatment. As used herein, the term is meant to encompass a person having or suspected of having a disease including a person who may be symptomatic for a disease but who has not yet been diagnosed.

BRIEF DESCRIPTION OF THE FIGURES

FIGS. 1A-C disclose SEQ ID NOS 1 and 32-33, respectively, in order of appearance.

DETAILED DESCRIPTION

Figure 1A:
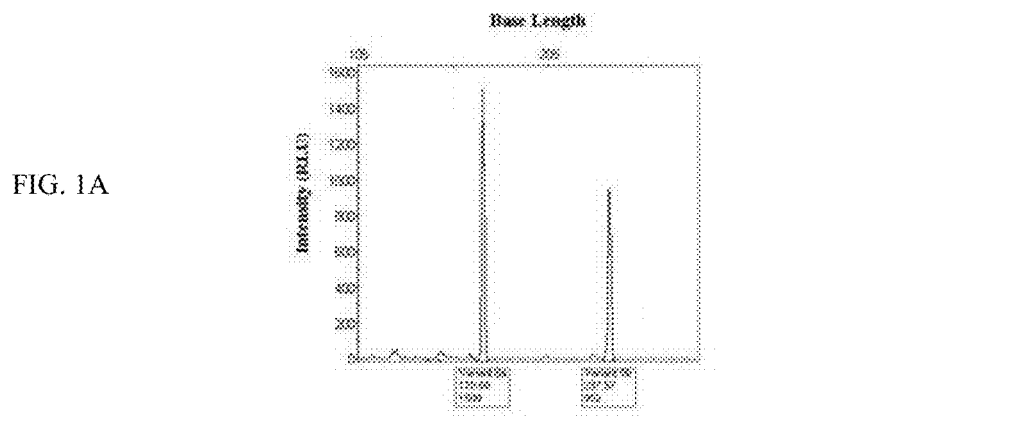
FIG. 1A is a chromatogram showing the results of amplifying RNA from FFPE tissue from a NSCLC patient using an unlableled EML4 exon 17 forward primer and FAM-labeled ALK exon 20 reverse primer. Two peaks were observed at position 171 bp and 238 bp, indicating presence of at least two fusion variants.
Figure 1B:
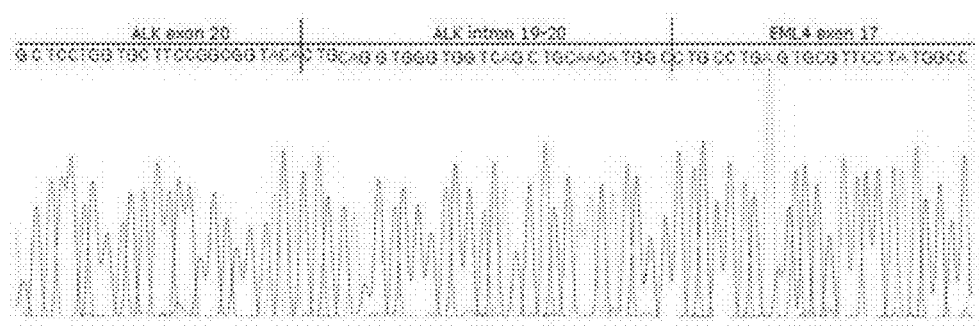
FIG. 1B and FIG. 1C are electropherograms from reverse sequencing reactions. The 171 bp peak (FIG. 1B) consisted of a complete EML4 exon 17 and ALK exon 20 separated by 30 bp of adjacent ALK intron 19-20 sequence and the 238 bp peak (FIG. 1C) also contains a complete EML4 exon 17 and ALK exon 20 and adjacent ALK intron 19-20 with an added 4 bp (boxed) of that intron and furthermore includes 61 bp of non-adjacent intron 17-18 separating EML4 exon 17 and ALK intron sequence.

In accordance with the present invention, methods are provided for detecting a particular nucleic acid segment of interest in a sample of nucleic acids. In particular embodiments, the nucleic acid segment of interest includes the junction of a fusion of the EML4-ALK genes. This information may be used to determine if an individual is suffering from or is susceptible to a neoplastic disorder, such as NSCLC.

In practicing the methods described herein, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N Y, 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Assays for the Detection of EML4-ALK Fusion Genes

In one aspect, the present methods are designed to detect various target nucleic acids associated with cancer, e.g., non-small cell lung cancer. In one embodiment, an assay for an EML4-ALK gene fusion involves detecting nucleic acid segments corresponding to the fusion gene that are relevant to a diagnosis of cancer. Nucleic acid segments may be detected in a variety of ways, which are described in further detail below. In one embodiment, an assay for EML4-ALK gene fusions may be performed using PCR or RT-PCR. In another embodiment, an assay for an EML4-ALK gene fusion involves detecting an aberrant protein.

In one embodiment, the EML4-ALK variant (designated "variant 8a") is a fusion between exon 20 of ALK and exon 17 of EML4 with an insertion of 30 nucleotides of ALK introns 19-20. According to the nomenclature of Horn and Pao, *J Clin Oncol* 27: 4232-4235 (2009), this variant would be named "E17; ins30A20". The sequence of variant 8a surrounding the breakpoint is set forth in SEQ ID NO: 1. Nucleotides 1-24 of SEQ ID NO: 1 represent the 3'-region of ALK exon 20. Nucleotides 55-78 of SEQ ID NO: 1 represent the 5'-region of EML4 exon 17. The underlined region (nucleotides 25-54) of SEQ ID NO: 1 is the 30 nucleotide insert from ALK introns 19-20.

```
                                         (SEQ ID NO: 1)
GCTCCTGGTG CTTCCGGCGG TACACTGCAG GTGGGTGGTC

AGCTGCAACA TGGCCTGCCT GAGTGCGTTC CTATGGCC
```

Thus, variant 8a may be detected by detecting the presence of the 5' insertion junction (CGGCGGTACA:CTGCAGGTGG; SEQ ID NO: 26), the 3'-insertion junction (GCAACATGGC:CTGCCTGAGT; SEQ ID NO: 27), or the entire insertion (underlined), wherein the colon indicates the junction between the intron 19-20 insertion and the exonic sequences. The presence of the 5'- and 3'-junctions (e.g., SEQ ID NOs: 26 and 27) or the full ALK intron 19-20 insertion may be assessed by any convenient method including nucleotide sequence and/or hybridization of an oligonucleotide probe that contains a sufficient number of nucleotides on either side of the junction in order that specific hybridization can be assessed. The simultaneous presence of both the 5'- and 3'-junctions (SEQ ID NOs: 26 and 27) in a single sample, or the ALK intron 19-20 insert alone (e.g., in mRNA) are indicative of variant 8a EML4-ALK translocation. The exemplary 20-mer sequences provided above, or complements thereof, may be used hybridization probes or otherwise may be used as target regions of interest for assessment of variant 8a.

In one embodiment, an EML4-ALK variant (designated "variant 8b") is a fusion between exon 20 of ALK and exon 17 of EML4 with an insertion of 95 nucleotides between the ALK and EML4 exons. The insertion sequence, in the 5'-to-3' direction consists of the same 30 nucleotides from ALK introns 19-20 as in variant 8a, a four nucleotide insert (CTGG), and 61 nucleotides from EML4 introns 17-18. According to the nomenclature of Horn and Pao, this variant would be named "E17ins30; ins65A20". The sequence of variant 8b surrounding the breakpoint is set forth in SEQ ID NO: 2. Nucleotides 1-24 of SEQ ID NO: 2 represent the 3'-region of ALK exon 20. Nucleotides 120-143 of SEQ ID NO: 2 represent the 5'-region of EML4 exon 17. The underlined region (nucleotides 25-54) of SEQ ID NO: 2 is the 30 nucleotide insert from ALK introns 19-20. The lower case nucleotides (nucleotides 55-58) is the four base insert. And, the bold, italicized nucleotides (nucleotides 59-119) is the inserted sequence from EML4 introns 17-18.

```
                                         (SEQ ID NO: 2)
GCTCCTGGTG CTTCCGGCGG TACACTGCAG GTGGGTGGTC

AGCTGCAACA TGGCctggCA GCATTCCACA TTTTTTAATG

AGTTTAATTT TGGGAAAATTGACTTCATGT TTTTGTCTCc

TGCCTGAGTG CGTTCCTATG GCC
```

Thus, variant 8b may be detected by detecting the present of the 5' insertion junction (e.g., SEQ ID NO: 26), the 3'-insertion junction (TTTTTGTCTC:CTGCCTGAGT; SEQ ID NO: 28), or the entire 95 bp insertion, wherein the colon indicates the junction between the intronic insertions and the exonic sequences. The presence of the 5'- and 3'-junctions (e.g., SEQ ID NOs: 26 and 28) or the full 95 bp insertion (or a diagnostic portion thereof) may be assessed by any convenient method including nucleotide sequence and/or hybridization of an oligonucleotide probe that contains a sufficient number of nucleotides on either side of the junction in order that specific hybridization can be assessed. The simultaneous presence of both the 5'- and 3'-junctions (SEQ ID NOs: 26 and 28) in a single sample, or the full 95 bp insertion (or a diagnostic portion thereof) (e.g., in mRNA) are indicative of variant 8b EML4-ALK translocation. The exemplary 20-mer sequences provided above, or complements thereof, may be used hybridization probes or otherwise may be used as target regions of interest for assessment of variant 8b.

In one aspect, the methods may detect two or more EML-ALK gene fusion variants, e.g., in a multiplex or multiple singleplex PCR assays. For instance the assay may detect variant 8a and/or variant 8b with one or more of the following variants: variant 1, variant 2, variant 3a, variant 3b, variant 4, variant 5a, variant 5b, variant 6, and variant 6. A description of these variants is set forth in Table 1, and are described further in Horn and Pao, *J Clin Oncol* 27: 4232-4235 (2009).

TABLE 1

EML4-ALK Fusion Variants

| Variant | Description |
| --- | --- |
| V1 (E13; A20) | Variant 1 fuses exon 13 of EML4 to exon 20 of ALK. |
| V2 (E20; A20) | Variant 2 fuses exon 20 of EML4 to exon 20 of ALK. |
| V3a (E6a; A20) | Variant 3a fuses exon 6a of EML4 to exon 20 of ALK. |
| V3b (E6b; A20) | Variant 3b fuses exon 6b of EML4 to exon 20 of ALK. |
| V4 (E14; ins11del49A20) | Variant 4 fuses exon 14 of EML4 with an additional 11 nucleotides of unknown origin to nucleotide 50 within exon 20 ALK. |
| V5a (E2; A20) | Variant 5a fuses exon 2 of EML4 to exon 20 of ALK. |
| V5b (E2; ins117A20) | Variant 5b fuses exon 2 of EML4 to intron 19 of ALK (including 117 nucleotides from intron 19). |
| V6 (E13; ins69A20) | Variant 6 fuses exon 13 of EML4 to intron 19 of ALK (including 69 nucleotides from intron 19). |
| V7 (E14; del12A20) | Variant 7 fuses exon 13 of EML4 to nucleotide 13 in within exon 20 of ALK. |
| V8a (E17; ins30A20) | Variant 8a fuses exon 17 of EML4 to intron 19 of ALK (including 35 nucleotides from intron 19). |
| V8b (E17ins30; ins65A20) | Variant 8b fuses exon 17 (with an addition 60 nucleotides from intron 18) of EML4 to intron 19 of ALK (including 35 nucleotides from intron 19). |

Exemplary RT-PCR primers for the detection of EML-ALK fusions are shown in Table 2 below. With regard to the exemplary primers and probes, those skilled in the art will readily recognize that nucleic acid molecules may be double-stranded molecules and that reference to a particular site on one strand refers, as well, to the corresponding site on a complementary strand. In defining a variant position, allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular variant position, allele, or nucleotide sequence. Probes and primers, may be designed to hybridize to either strand and detection methods disclosed herein may generally target either strand.

Sample Collection and Preparation

The methods and compositions of this invention may be used to detect nucleic acids associated with various EML4-ALK gene fusions using a biological sample obtained from an individual. The nucleic acid (DNA or RNA) may be isolated from the sample according to any methods well known to those of skill in the art. Biological samples may be obtained by standard procedures and may be used immediately or stored, under conditions appropriate for the type of biological sample, for later use.

Starting material for the detection assays is typically a clinical sample, which is suspected to contain the target nucleic acids. An example of a clinical sample is a tissue from a biopsy. Next, the nucleic acids may be separated from proteins and sugars present in the original sample. Any purification methods known in the art may be used in the context of the present invention. Nucleic acid sequences in the sample can successfully be amplified using in vitro amplification, such as PCR. Typically, any compounds that may inhibit polymerases are removed from the nucleic acids.

Methods of obtaining test samples are well known to those of skill in the art and include, but are not limited to, aspirations, tissue sections, swabs, drawing of blood or other fluids, surgical or needle biopsies, and the like. The test sample may be obtained from an individual or patient. The test sample may contain cells, tissues or fluid obtained from a patient suspected being afflicted with or cancer, e.g., NSCLC. The test sample may be a cell-containing liquid or a tissue. Samples may include, but are not limited to, cells from a vaginal swab, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the cells in the sample to detect using polymerase chain reaction.

Nucleic Acid Extraction and Amplification

The nucleic acid to be amplified may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France).

Nucleic acid extracted from cells or tissues can be amplified using nucleic acid amplification techniques well known in the art. By way of example, but not by way of limitation, these techniques can include the polymerase chain reaction (PCR), reverse transcriptase polymerase chain reaction (RT-PCR), nested PCR, ligase chain reaction. See Abravaya, K., et al., *Nucleic Acids Research*, 23:675-682, (1995), branched DNA signal amplification, Urdea, M. S., et al., *AIDS*, 7 (suppl 2):S11-S14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods*, 35:273-286, (1991), Invader Technology, or other sequence replication assays or signal amplification assays may also be used. These methods of amplification are each described briefly below and are well-known in the art.

Some methods employ reverse transcription of RNA to cDNA. The method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

LCR is a method of DNA amplification similar to PCR, except that it uses four primers instead of two and uses the enzyme ligase to ligate or join two segments of DNA. LCR can be performed as according to Moore et al., *J Clin Micro*, 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, Chicago, IL).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS*, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 min for the synthesis of RNA. The above steps are then repeated. Alternatively, after the initial cDNA synthesis, both RT and RNA polymerase are added following a 1 min 100° C. denaturation followed by an RNA elongation of approximately 30 min at 37° C. TAS can be also be performed on solid phase as according to Wylie et al., *J Clin Micro*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *E. coli* Rnase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *E. coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *Eur J Biochem*, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo$^-$ Klenow polymerase). The sample mixture is heated 95° C. for 4 min to denature target DNA prior to addition of the enzymes. After addition of the two enzymes, amplification is carried out for 120 min at 37° C. in a total volume of 50 µl. Then, the reaction is terminated by heating for 2 min at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi, *Trends Biotechnol.*, 1991 9(2):53-8, 1991).

In suitable embodiments, PCR is used to amplify a target sequence of interest. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan et al., *J of Clin Micro*, 33(3):556-561 (1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity. Exemplary primers for detecting EML4-ALK gene fusion by RT-PLR are set forth in Table 2.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866, 336 and 6,117,635).

Nucleic acids may be amplified prior to detection or may be detected directly during an amplification step (i.e., "real-time" methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

In one embodiment, detection of a target nucleic acid, such as a nucleic acid from an EML4-ALK gene fusion, is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the target nucleic acids are useful in diagnostic assays for neoplastic disorders, such as NSCLC, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

Other methods of probe hybridization detected in real time can be used for detecting amplification of a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in some embodiments, amplified fractions are separated on an agarose gel and stained with ethidium bromide by methods known in the art to detect amplified fragments.

As a quality control measure, an internal amplification control may be included in one or more samples to be extracted and amplified. The skilled artisan will understand that any detectable sequence that is not typically present in the sample can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Protein Assays

In one aspect, the present invention provides methods of detecting a mutant protein associated with a neoplastic disorder, such as NSCLC. In one embodiment, the methods provide for detection of an EML4-ALK fusion protein. The presence of EML4-ALK fusion proteins can be measured by immunoassay, using antibodies specific for the mutant protein. Lack of antibody binding would indicate the absence of mutant EML4-ALK molecules and suggest that the subject does not have or is not susceptible to a neoplastic disorder associated with the mutant EML4-ALK protein. Antibodies specific to wild-type EML4 or ALK protein may be used as a control.

Antibodies which are specifically reactive with mutant EML4-ALK proteins may be obtained in a number of ways which will be readily apparent to those skilled in the art. The fusion protein can be produced in a recombinant system using the mutant nucleotide sequence. The recombinant protein can be injected into an animal as an immunogen to elicit polyclonal antibody production. The resultant polyclonal antisera may be used directly or may be purified by, for example, affinity absorption using recombinantly produced EML4-ALK fusion proteins coupled to an insoluble support.

In another alternative, monoclonal antibodies specifically immunoreactive with the fusion protein may be prepared according to well known methods (See, e.g., Kohler and Milstein, 1976, Eur. J. Immunol., 6:611), using a peptide as an immunogen, using it for selection or using it for both functions. These and other methods for preparing antibodies that are specifically immunoreactive with the recombinant protein of this invention are easily within the skill of the ordinary worker in the art. Suitably, antibodies specific for mutant EML4-ALK fusion protein will not react with normal (wild type) EML4 or ALK proteins. Similar methods can be used to produce antibodies specifically immunoreactive with wild-type EML4 or ALK.

Kits

In a further aspect, the invention disclosure provides kits for diagnosing a neoplastic disorder in an individual, the kit comprising: a set of reagents for determining the presence or absence, or differential presence, of EML4-ALK gene fusions. In one embodiment, at least one primer pair is selected from the group consisting of: SEQ ID NOs: 3/25, 4/25, 5/25, 6/25, 7/25, 8/25, 9/25, 10/25, 11/25, 12/25, 13/25; 16/25, 17/25, 18/25, 19/25, 20/25, 21/25, 22/25, 23/25, and 24/25. In one embodiment, the kit contains one or more of the primers of SEQ ID NOs: 3-28.

EXAMPLE

The present invention is further illustrated by the following examples, which should not be construed as limiting in any way.

Example 1: Cytogenetic Analysis

FFPE sections 4-5 µm in size were used for FISH with an ALK dual-color break-apart probe (Abbott Molecular, Inc., Des Plaines, IL); the slides were deparaffinized prior to probe application. FISH analysis was performed using a Nikon 50i fluorescence microscope (Nikon Corp., Tokyo, Japan). The images were captured using a CCD camera and Isis® imaging system (MetaSystems Group, Inc., Watertown, MA). Unstained slides were deparaffinized and stained with CONFIRM™ anti-ALK1 primary antibody (mouse monoclonal clone ALK01; Ventana Medical Systems, Tucson AZ). All immunohistochemistry steps were performed using the BenchMark XT, according to manufacturer's protocol (Ventana Medical Systems, Tucson, AZ).

Cytogenetic analysis of a non-small cell lung cancer (NSCLC) patient revealed breakage within the ALK gene. Both haploid and diploid cells were observed where split signal from the 5' and 3' ALK probes were evident. Likewise, immunohistochemistry of the tissue sample confirmed significant ALK1 staining indicating overexpression of ALK1 in the malignant cells.

Example 2: Evaluation of EML4-ALK Fusions

Because the FISH and IHC results from Example 1 indicated an oncogenic ALK1 rearrangement, the molecular characteristics were further investigated under the assumption that there was an EML4-ALK fusion event. RT-PCR amplification with primers to detect the first 11 published EML4-ALK fusion variants (variant 1, 2, 3a, 3b, 4, 5a, 5b, 6, and 7) yielded results that suggested the likely involvement of a previously undescribed EML4-ALK fusion variant (s).

Methods. Sixty (60) patient samples were analyzed with the multiplex assay: 55 formalin-fixed paraffin-embedded (FFPE) NSCLC samples (37 patients with adenocarcinoma, 11 squamous cell carcinoma, 5 adenosquamous cell carcinoma and 2 large cell carcinomas), 4 cell line samples (3 NSCLC; 1 Prostate Cancer), and 1 control RNA (Human Total RNA, Applied Biosystems). Tissue blocks were sectioned onto slides for H&E staining or unstained for RNA extraction. Tumor area was identified by a licensed pathologist and tissue from this area was scraped for RNA extraction with HighPure miRNA Isolation kit (Roche Applied Science, Mannheim, Germany). RNA was DNase I digested with DNA-free (Applied Biosystems/Ambion, Austin TX) prior to amplification.

After RNA extraction, RT-PCR was performed using the RNA UltraSense™ One-Step qRT-PCR System (Invitrogen, Carlsbad, CA). 23 primers (22 unlabeled EML4 forward; 1 FAM labeled ALK reverse) were included in 4 master mixes to amplify EML4-ALK fusions initiating within the first 22 EML4 exons to ALK exon 20 (Table 2). One endogenous control (beta-2-microglobulin) primer set was included in a separate reaction. Thermocycling was performed as follows: RNA reverse transcribed by incubation at 55° C. for 30 min followed by denaturing step at 94° C. for 2 min; PCR amplification performed by 40 cycles of denaturation at 94° C. for 15 see; annealing at 60° C. for 30 min; extension at 68° C.; and final extension at 68° C. for 5 min following cycling. RT-PCR to query alternative splicing in intron 17 was performed as above, with exception that the annealing temperature was 50° C. Exemplary primers include:

TABLE 2

Exemplary RT-PCR Primers for Detecting EML4-ALK Gene Fusions

| Primer Target | Sequence (5' to 3') | SEQ ID NO: |
|---|---|---|
| EML4 Exon 1 (Forward) | CGGTCCGCTGAATGAAGT | SEQ ID NO: 3 |
| EML4 Exon 2 (Forward) | AAGATCATGTGGCCTCAGTG | SEQ ID NO: 4 |
| EML4 Exon 3 (Forward) | TGGTGCAAACAGAAAACCAA | SEQ ID NO: 5 |
| EML4 Exon 4 (Forward) | CCCTCTTCACAACCTCTCCA | SEQ ID NO: 6 |
| EML4 Exon 5 (Forward) | ACGACCATCACCAGCTGAAA | SEQ ID NO: 7 |

TABLE 2-continued

Exemplary RT-PCR Primers for Detecting EML4-ALK Gene Fusions

| Primer Target | Sequence (5' to 3') | SEQ ID NO: |
|---|---|---|
| EML4 Exon 6 (Forward) | CTGCAGACAAGCATAAAGATG | SEQ ID NO: 8 |
| EML4 Exon 7 (Forward) | GTCGGCCAATTACCATGTTC | SEQ ID NO: 9 |
| EML4 Exon 8 (Forward) | CTTCCGACCGGGAAAATAGT | SEQ ID NO: 10 |
| EML4 Exon 9 (Forward) | ACATCCTGACAAAATTAGGATTGC | SEQ ID NO: 11 |
| EML4 Exon 10 (Forward) | CCTCTACAACCCCACGTCAG | SEQ ID NO: 12 |
| EML4 Exon 11 (Forward) | GCATATGCTTACTGTATGGGACTG | SEQ ID NO: 13 |
| EML4 Exon 12 (Forward) | TTTCACCCAACAGATGCAAA | SEQ ID NO: 14 |
| EML4 Exon 13 (Forward) | GACTCAGGTGGAGTCATGC | SEQ ID NO: 15 |
| EML4 Exon 14 (Forward) | AAGCTCATGATGGCAGTGTG | SEQ ID NO: 16 |
| EML4 Exon 15 (Forward) | TGTAGCAGAAGGAAAGGCAGA | SEQ ID NO: 17 |
| EML4 Exon 16 (Forward) | GTCTTGCCACACATCCCTTC | SEQ ID NO: 18 |
| EML4 Exon 17 (Forward) | CCAGGACACTGTGCAGATTT | SEQ ID NO: 19 |
| EML4 Exon 18 (Forward) | AGGTGGTTTGTTCTGGATGC | SEQ ID NO: 20 |
| EML4 Exon 19 (Forward) | CCTTCCTGGCTGTAGGATCTC | SEQ ID NO: 21 |
| EML4 Exon 20 (Forward) | CAGATATGGAAGGTGCACTG | SEQ ID NO: 22 |
| EML4 Exon 21 (Forward) | ATTCCAAATGGCTGCAAACT | SEQ ID NO: 23 |
| EML4 Exon 22 (Forward) | AGCTGTTGCCGATGACTTTT | SEQ ID NO: 24 |
| ALK Exon 20 (Reverse) | AGCTTGCTCAGCTTGTACTC | SEQ ID NO: 25 |

RT-PCR products were diluted 1:10 with $H_2O$, denatured in formamide containing ROX GeneScan 350 size marker (Applied Biosystems, Foster City CA), and size fractionated by capillary electrophoresis in an ABI 3730 Genetic Analyzer (Applied Biosystems, Foster City CA). Results were analyzed by GeneMapper Software (Applied Biosystems, Foster City CA). Samples with positive results were further analyzed by singleplex RT-PCR to confirm exon involvement and novel fusions were confirmed by direct sequencing.

For cDNA sequencing, RT-PCR products were separated by capillary electrophoresis on a 200 agarose gel. Individual bands were cut out of the gel and DNA extracted by MinElute Gel Extraction Kit, according to manufacturer's instructions (Qiagen, Valencia CA). Forward and reverse primers used in RT-PCR served as forward and reverse primers for sequencing using ABI Prism Big Dye Terminator v3.1 Cycle Sequencing Kit, according to manufacturer's instructions (Applied Biosystems, Foster City CA).

For immunohistochemistry, unstained slides were deparaffinized and stained with CONFIRM™ anti-ALK1 primary antibody (mouse monoclonal clone ALK01; Ventana Medical Systems, Tucson AZ). All immunohistochemistry steps were performed using the BenchMark XT, according to manufacturer's protocol (Ventana Medical Systems, Tucson AZ).

Results: A fluorescent RT-PCR assay was designed utilizing a single FAM-labeled ALK exon 20 reverse primer and 22 forward primers for each of the first 22 exons of EML4 (Table 2). The forward primers were split into 4 separate reactions, all containing the labeled ALK exon 20 reverse primer. Upon fragment analysis, each known EML4-ALK fusion variant would yield a specific size that is utilized to identify the fusion(s) present. Furthermore, potential exon fusions would yield a unique size product for ease of identification of EML4 exon involvement, assuming no insertions or deletions are present (Table 3).

TABLE 3

Expected amplicon size by variant

| EML4/ALK variant | EML4 exon involvement | Multiplex Reaction# | Amplicon Size (bp) |
|---|---|---|---|
| Published EML4-ALK fusion variants | | | |
| 2, 3a, 3b, 4, 7, E20; ins18A20 | 20, 6, 14, 20 | 1 | 183, 112, 145, 163, 187, 201 |
| "V5" | 18 | 2 | 167 |
| 1, 6, E17;ins68A20 | 13, 17 | 3 | 146, 215, 144 |
| "V4", 5a, 5b | 15, 2 | 4 | 134, 118, 235 |
| Potential EML4 exon involvement* | | | |
| Unknown | 1, 5, 9, 12, 16, 21 | 2 | 152, 199, 137, 181, 186, 170 |
| Unknown | 3, 7, 10, | 3 | 154, 170, 187, |
| Unknown | 4, 8, 11, 19, 22 | 4 | 144, 183, 131, 168, 137 |

*Amplicon sizes are estimated based on no insertions or deletions

Screening of 55 NSCLC formalin-fixed paraffin embedded (FFPE) tumor tissue samples resulted in detection of 9.1% (5/55) EML4-ALK fusion positive cases, all of which were classified as adenocarcinoma (Table 4). Four of the positive cases harbored previously described fusion variants, the majority of which were variants 3a and/or 3b (3/5) and one variant 1 (Table 5).

TABLE 4

Distrubution of EML4-ALK positive tumors by NSCLC subtype.

| Subtype | n | EML4-ALK Positive |
|---|---|---|
| Total | 55 | 9.1% (5/55) |
| Adenocarcinoma | 37 | 13.5% (5/37) |
| Squamous cell | 11 | 0% |
| Adenosquamous | 5 | 0% |
| Large cell carcinoma | 2 | 0% |

TABLE 5

Distribution of EML4-ALK fusion variants.

| EML4-ALK | Positive | Variant Reference |
|---|---|---|
| Total | 9.1% (5/55) | See below |
| Variant 1 | 1.8% (1/55) | Soda et al., 2007 |
| Variant 2 | 0% | Soda et al., 2007 |
| Variant 3a | 5.3% (3/55) | Choi et al., 2008 |
| Variant 3b | 3.5% (2/55) | Choi et al., 2008 |
| Variant 4 | 0% | Takeuchi et al., 2008 |
| Variant "4" | 0% | Koivunen et al., 2008 |
| Variant 5a | 0% | Takeuchi et al., 2008 |
| Variant 5b | 0% | Takeuchi et al., 2008 |
| Variant "5" | 0% | Wong et al., 2009 |
| Variant 6 | 0% | Takeuchi et al., 2009 |
| Variant 7 | 0% | Takeuchi et al., 2009 |
| Variant 8a | 1.8% (1/55) | Present study |
| Variant 8b | 1.8% (1/55) | Present study |
| Variant E17 | 0% | Tokahashi et al., 2009 |
| Variant E20 | 0% | Tokahashi et al., 2009 |

In addition, one case yielded 2 strong amplification peaks at unexpected sizes in the reaction containing EML4 exon 3, 7, 10, 13, and 17 (master mix #3). In order to identify the EML4 exon involvement, separation of the primers into individual reactions revealed that both peaks resulted from amplification with the EML4 exon 17 forward primer yielding 2 amplicons of 170 bp and 237 bp (FIG. 1A). ALK rearrangement was also confirmed by fluorescence in situ hybridization (FISH) using break apart probes to detect rearrangements at the 2p23 locus. Both haploid and diploid cells were observed in the specimen harboring novel variants 8a/b, where split signal from the 5' and 3' ALK probes were evident (data not shown).

Twenty-two additional specimens (3 more EML4-ALK positive and 19 negative by RT-PCR) were also confirmed by FISH as described above for a total of 23 of the 55 specimens (data not shown). Due to limited sample, FISH was not performed on the variant 1 positive specimen. All specimens that tested negative by RT-PCR also tested negative by FISH. Three of the four total RT-PCR positives tested were also positive by FISH. One sample tested positive for EML4-ALK fusion variants 3a and 3b by RT-PCR, but negative for by FISH. Upon repeat RNA extraction and RT-PCR, detection of variant 3a and 3b in this specimen by RT-PCR was duplicated. These results suggest higher sensitivity of the RT-PCR assay.

Figure 1C:
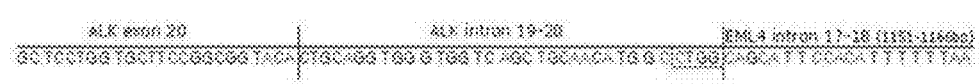
Figure 1C:
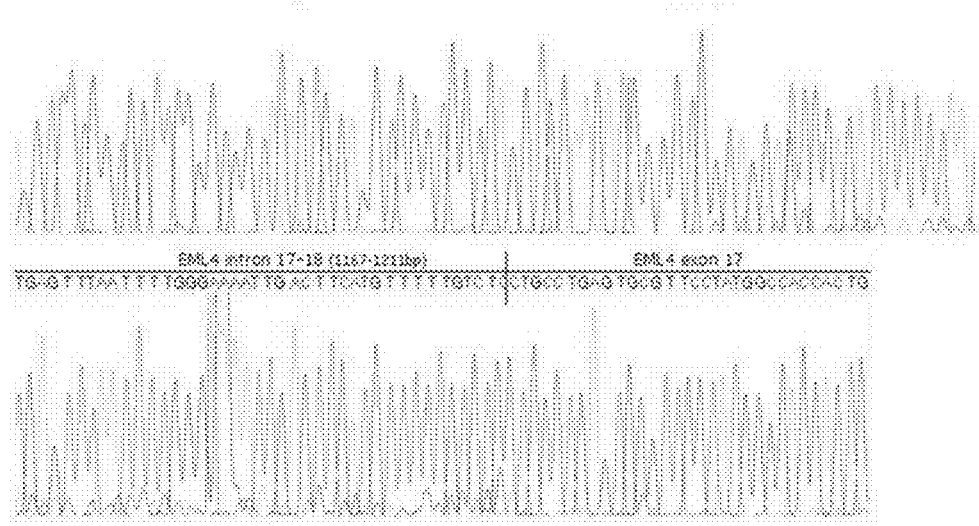
Figure 2A:
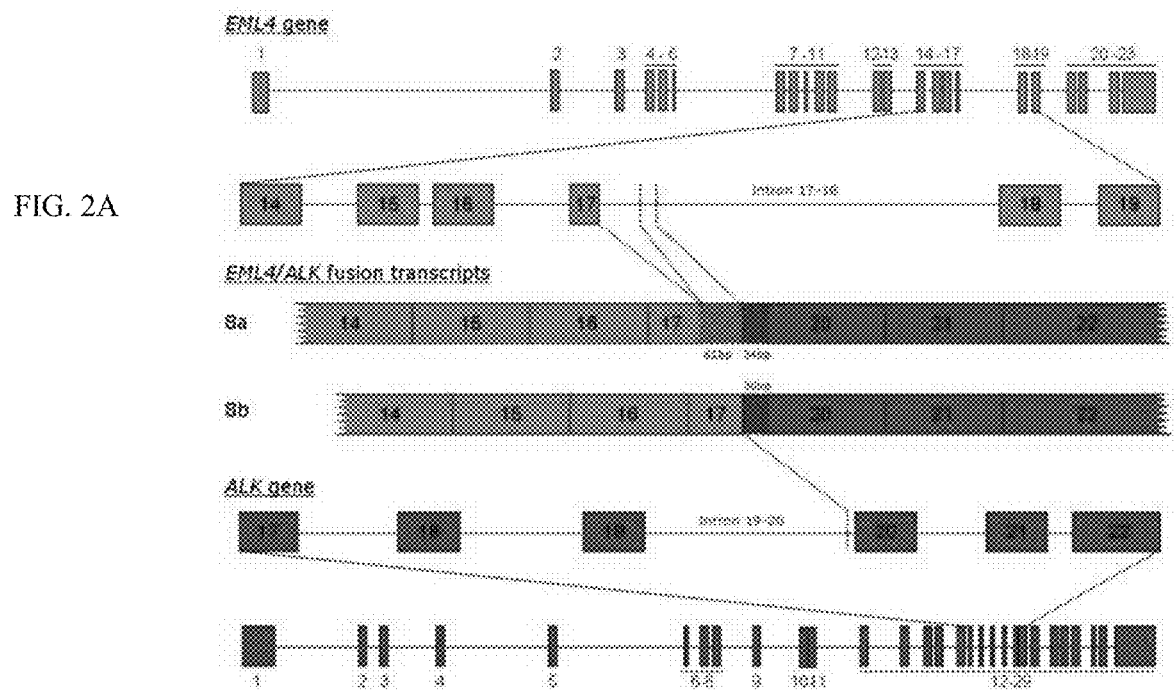
FIG. 2A and FIG. 2B are schematic diagrams of fusion transcripts resulting from EML4 (light) and ALK (dark) genetic rearrangement of the EML4-ALK variants 8a and 8b, respectively. Intronic sequences carried over to the fusion transcripts are indicated by dotted lines. Putative EML4 truncation containing the N-terminal region of EML4 consisting of HELP and partial WD repeat domains (variant 8a) and fusion of the N-terminal region of EML4 to the C-terminal region of ALK containing the protein tyrosine kinase domain (variant 8b). Breakpoints indicated with a dotted line. IDS, intron-derived sequence; TM, transmembrane domain.

Sequencing of the un-identified amplicons described above demonstrated that both amplicons were composed of complete EML4 exon 17 and ALK exon 20, differing in size based on varying partial intron insertions. The 170 bp peak (variant 8a) consisted of EML4 exon 17 fused to ALK exon 20 containing a 30 nucleotide intron 19 insertion, E17; ins30A20 (FIG. 1). The 237 bp peak (variant 8b) consisted of EML4 exon 17, with an insertion of 61 non-adjacent nucleotides from intron 17, fused to ALK exon 20 with a 34 nucleotide insertion from intron 19, E17ins61; ins34A20 (FIG. 1C). As a result, the two fusion products formed likely consist of EML4 exon 1-17 and ALK 20-29 with a 30 bp (8a) or 95 bp (8b) insertion (FIG. 2A).

In order to determine whether the EML4 intron 17 segment may be observed adjacent to exon 17 as a result of alternative splicing in normal EML4 transcripts, RT-PCR was performed on 3 NSCLC cell lines (NCI-H2228, NCI-1299, NCI-H838), two normal lung cancer tissues and the variant 8a/b positive lung cancer tissue using primers specific to exon 17 and the 61 bp intron 17 segment. The only specimen that resulted in an amplicon of expected size was the variant 8a/b positive lung cancer specimen (data not shown). This suggests that as a result of this specific paracentric inversion, a new alternative splice site is created in the pre-mRNA transcript.

Figure 2B:
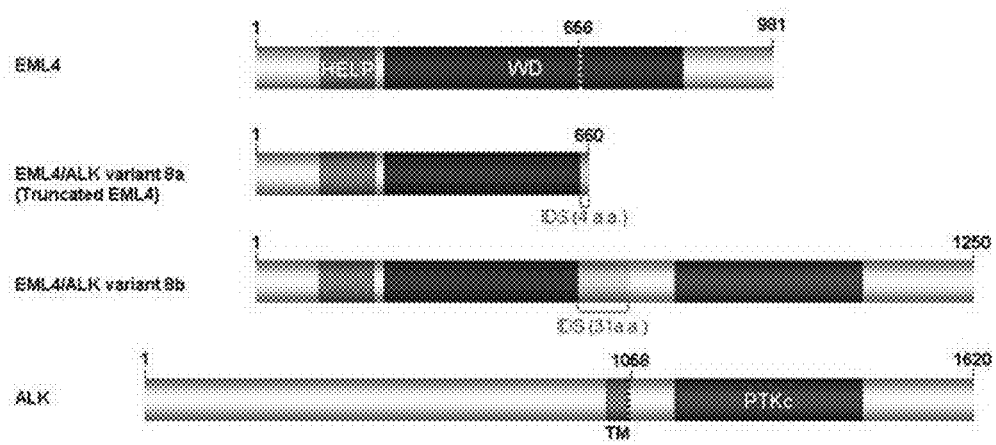

Based on the deduced amino acid sequence, the translated variant 8a protein yields a 660 a.a. protein (SEQ ID NO: 29) and variant 8b yields a 1250 a.a. protein (SEQ ID NO: 30), shown below. Fusion variant 8a appears to encode an EML4 truncation with no functional ALK domains resulting from the presence of an early stop codon located in the 30 bp insertion (FIG. 2B). However, variant 8b contains an in-frame 95 bp insertion resulting in the presence of a putatively functional ALK protein tyrosine kinase domain (underlined amino acids in SEQ ID NO: 30 below). (See FIG. 2B).

```
                                          (SEQ ID NO: 29)
MDGFAGSLDDSISAASTSDVQDRLSALESRVQQQEDEITVLKAALADVLR
RLAISEDHVASVKKSVSSKGQPSPRAVIPMSCITNGSGANRKPSHTSAVS
IAGKETLSSAAKSGTEKKKEKPQGQREKKEESHSNDQSPQIRASPSPQPS
SQPLQIHRQTPESKNATPTKSIKRPSPAEKSHNSWENSDDSRNKLSKIPS
TPKLIPKVTKTADKHKDVIINQEGEYIKMFMRGRPITMFIPSDVDNYDDI
RTELPPEKLKLEWAYGYRGKDCRANVYLLPTGEIVYFIASVVVLFNYEER
TQRHYLGHTDCVKCLAIHPDKIRIATGQIAGVDKDGRPLQPHVRVWDSVT
LSTLQIIGLGTFERGVGCLDFSKADSGVHLCVIDDSNEHMLTVWDWQKKA
KGAEIKTTNEVVLAVEFHPTDANTIITCGKSHIFFWTWSGNSLTRKQGIF
GKYEKPKFVQCLAFLGNGDVLTGDSGGVMLIWSKTTVEPTPGKGPKGVYQ
ISKQIKAHDGSVFTLCQMRNGMLLTGGGKDRKIILWDHDLNPEREIEVPD
QYGTIRAVAEGKADQFLVGTSRNFILRGTFNDGFQIEVQGHTDELWGLAT
HPFKDLLLTCAQDRQVCLWNSMEHRLEWTRLVDEPGHCADFHPSGTVVAI
GTHSGRPCCS (SEQ ID NO: 30)
MDGFAGSLDDSISAASTSDVQDRLSALESRVQQQEDEITVLKAALADVLR
RLAISEDHVASVKKSVSSKGQPSPRAVIPMSCITNGSGANRKPSHTSAVS
IAGKETLSSAAKSGTEKKKEKPQGQREKKEESHSNDQSPQIRASPSPQPS
SQPLQIHRQTPESKNATPTKSIKRPSPAEKSHNSWENSDDSRNKLSKIPS
TPKLIPKVTKTADKHKDVIINQEGEYIKMFMRGRPITMFIPSDVDNYDDI
RTELPPEKLKLEWAYGYRGKDCRANVYLLPTGEIVYFIASVVVLFNYEER
TQRHYLGHTDCVKCLAIHPDKIRIATGQIAGVDKDGRPLQPHVRVWDSVT
LSTLQIIGLGTFERGVGCLDFSKADSGVHLCVIDDSNEHMLTVWDWQKKA
KGAEIKTTNEVVLAVEFHPTDANTIITCGKSHIFFWTWSGNSLTRKQGIF
GKYEKPKFVQCLAFLGNGDVLTGDSGGVMLIWSKTTVEPTPGKGPKGVYQ
ISKQIKAHDGSVFTLCQMRNGMLLTGGGKDRKIILWDHDLNPEREIEVPD
QYGTIRAVAEGKADQFLVGTSRNFILRGTFNDGFQIEVQGHTDELWGLAT
HPFKDLLLTCAQDRQVCLWNSMEHRLEWTRLVDEPGHCADFHPSGTVVAI
GTHSGRRQKHEVNFPKIKLIKKCGMLPGHVAADHPPAVYRRKHQELQAMQ
MELQSPEYKLSKLRTSTIMTDYNPNYCFAGKTSSISDLKEVPRKNITLIR
GLGHGAFGEVYEGQVSGMPNDPSPLQVAVKTLPEVCSEQDELDELMEALI
ISKENHQNIVRCIGVSLQSLPRFILLELMAGGDLKSFLRETRPRPSQPSS
LAMLDLLHVARDIACGCQYLEENHFIHRDIAARNCLLTCPGPGRVAKIGD
FGMARDIYRASYYRKGGCAMLPVKWMPPEAFMEGIFTSKTDTWSFGVLLW
EIFSLGYMPYPSKSNQEVLEFVTSGGRMDPPKNCPGPVYRIMTQCWQHQP
EDRPNFAIILERIEYCTQDPDVINTALPIEYGPLVEEEEKVPVRPKDPEG
VPPLLVSQQAKREEERSPAAPPPLPTTSSGKAAKKPTAAEISVRVPRGPA
VEGGHVNMAFSQSNPPSELHKVHGSRNKPTSLWNPTYGSWFTEKPTKKNN
PIAKKEPHDRGNLGLEGSCTVPPNVATGRLPGASLLLEPSSLTANMKEVP
LFRLRHFPCGNVNYGYQQQGLPLEAATAPGAGHYEDTILKSKNSMNQPGP
```

To determine whether a functional EML4-ALK fusion protein was present in the tumor tissue, immunohistochemistry (IHC) of the tissue with ALK1 monoclonal antibodies was performed. IHC confirmed significant ALK1 staining of the cytoplasm in tumor cells, indicating overexpression of the ALK domain of the fusion protein in the malignant cells (data not shown). Furthermore, nine additional specimens (1 more positive and 8 negative by RT-PCR) were confirmed by IHC for a total of 10 of the 55 specimens. In total, 2 RT-PCR positive cases were also positive by IHC and 8 RT-PCR negative cases were also negative by IHC.

Using this method to screen a relatively small cohort of NSCLC specimens (n=55) we were able to identify three previously described EML4-ALK fusion variants (1, 3a and 3b) as well as an additional two novel variants involving exon 17 of EML4 (8a and 8b) in 9.1% (5/55) of the NSCLC specimens examined. Notably, EML4 exon 17 to ALK exon 20 fusions will not yield an in-frame fusion unless they possesses insertions or deletions to create an in-frame fusion. In fact, one fusion variant that we observed (8a) contained an insertion of 30 bp that results in an early stop codon and would not likely have malignant transforming activity on its own. This particular case also expressed variant 8b, with a 95 bp insertion, which is most likely responsible for expression of the ALK domain in this specimen as observed by IHC and the transformation or malignant phenotype.

An interesting feature of variant 8b was the presence of a 61 bp sequence of non-adjacent EML4 intron 17. This intron sequence is located ~1.2 kb down stream of exon 17 in the normal EML4 transcript. Based on analysis of normal lung tissue and non-variant 8b containing cells, it is clear that this configuration of intron 17 is not a result of normal alternative splicing but rather alternative splicing that appears as a result of translocation.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for determining the EML4-ALK gene fusion variant status in a subject comprising:
   (a) obtaining a biological sample from a subject suspected of having or having a neoplastic disorder;
   (b) extracting nucleic acids from the biological sample to generate an isolated nucleic acid sample;
   (c) performing a multiplex reaction to amplify a plurality of nucleic acids in the isolated nucleic acid sample using oligonucleotide primers that bind to exons 1-22 of EML4 and exon 20 of ALK, wherein the oligonucleotide primers comprise at least 22 forward primers selected from SEQ ID NOs: 3-24; and
   (d) detecting the presence or absence of a EML4-ALK gene fusion variant in the amplified nucleic acids.

2. The method of claim 1, wherein detecting the EML4-ALK gene fusion variants comprises sequencing the amplified nucleic acids.

3. The method of claim 1, wherein the plurality of nucleic acids comprises SEQ ID NO: 1 or SEQ ID NO: 2.

4. The method of claim 1, wherein the oligonucleotide primers further comprise at least 1 reverse primer.

5. The method of claim 4, wherein the reverse primer is SEQ ID NO: 25.

6. The method of claim 1, wherein the neoplastic disorder is non-small lung cancer.

7. The method of claim 1, wherein the sample is selected from plasma, serum, or biopsy tissue.

8. The method of claim 1, wherein the EML4-ALK gene fusion variant is selected from variant V1, variant V2, variant V3a, variant V3b, variant V4, variant V5a, variant V5b, variant V6, variant V7, variant V8a, or variant V8b.

* * * * *

SEQUENCE LISTING

```
Sequence total quantity: 33
SEQ ID NO: 1            moltype = DNA  length = 78
FEATURE                 Location/Qualifiers
source                  1..78
                        mol_type = other DNA
                        organism = synthetic construct
                        note = Description of Artificial Sequence: Synthetic
                          oligonucleotide
SEQUENCE: 1
gctcctggtg cttccggcgg tacactgcag gtgggtggtc agctgcaaca tggcctgcct   60
gagtgcgttc ctatggcc                                                 78

SEQ ID NO: 2            moltype = DNA  length = 143
FEATURE                 Location/Qualifiers
source                  1..143
                        mol_type = other DNA
                        organism = synthetic construct
                        note = Description of Artificial Sequence: Synthetic
                          polynucleotide
SEQUENCE: 2
gctcctggtg cttccggcgg tacactgcag gtgggtggtc agctgcaaca tggcctggca   60
gcattccaca tttttaatg agtttaattt tgggaaaatt gacttcatgt ttttgtctcc   120
tgcctgagtg cgttcctatg gcc                                          143

SEQ ID NO: 3            moltype = DNA  length = 18
FEATURE                 Location/Qualifiers
```

```
source                  1..18
                        mol_type = other DNA
                        organism = synthetic construct
                        note = Description of Artificial Sequence: Synthetic primer
SEQUENCE: 3
cggtccgctg aatgaagt                                                    18

SEQ ID NO: 4            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 4
aagatcatgt ggcctcagtg                                                  20

SEQ ID NO: 5            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 5
tggtgcaaac agaaaaccaa                                                  20

SEQ ID NO: 6            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 6
ccctcttcac aacctctcca                                                  20

SEQ ID NO: 7            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 7
acgaccatca ccagctgaaa                                                  20

SEQ ID NO: 8            moltype = DNA  length = 21
FEATURE                 Location/Qualifiers
source                  1..21
                        mol_type = other DNA
                        organism = synthetic construct
                        note = Description of Artificial Sequence: Synthetic primer
SEQUENCE: 8
ctgcagacaa gcataaagat g                                                21

SEQ ID NO: 9            moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 9
gtcggccaat taccatgttc                                                  20

SEQ ID NO: 10           moltype = DNA  length = 20
FEATURE                 Location/Qualifiers
source                  1..20
                        mol_type = other DNA
                        organism = synthetic construct
                        note = Description of Artificial Sequence: Synthetic primer
SEQUENCE: 10
cttccgaccg ggaaaatagt                                                  20

SEQ ID NO: 11           moltype = DNA  length = 24
FEATURE                 Location/Qualifiers
source                  1..24
                        mol_type = other DNA
                        organism = synthetic construct
                        note = Description of Artificial Sequence: Synthetic primer
SEQUENCE: 11
acatcctgac aaaattagga ttgc                                             24
```

```
SEQ ID NO: 12          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 12
cctctacaac cccacgtcag                                                    20

SEQ ID NO: 13          moltype = DNA  length = 24
FEATURE                Location/Qualifiers
source                 1..24
                       mol_type = other DNA
                       organism = synthetic construct
                       note = Description of Artificial Sequence: Synthetic primer
SEQUENCE: 13
gcatatgctt actgtatggg actg                                               24

SEQ ID NO: 14          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 14
tttcacccaa cagatgcaaa                                                    20

SEQ ID NO: 15          moltype = DNA  length = 19
FEATURE                Location/Qualifiers
source                 1..19
                       mol_type = other DNA
                       organism = synthetic construct
                       note = Description of Artificial Sequence: Synthetic primer
SEQUENCE: 15
gactcaggtg gagtcatgc                                                     19

SEQ ID NO: 16          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 16
aagctcatga tggcagtgtg                                                    20

SEQ ID NO: 17          moltype = DNA  length = 21
FEATURE                Location/Qualifiers
source                 1..21
                       mol_type = other DNA
                       organism = synthetic construct
                       note = Description of Artificial Sequence: Synthetic primer
SEQUENCE: 17
tgtagcagaa ggaaaggcag a                                                  21

SEQ ID NO: 18          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 18
gtcttgccac acatcccttc                                                    20

SEQ ID NO: 19          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 19
ccaggacact gtgcagattt                                                    20

SEQ ID NO: 20          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 20
```

```
aggtggtttg ttctggatgc                                                   20

SEQ ID NO: 21           moltype = DNA   length = 21
FEATURE                 Location/Qualifiers
source                  1..21
                        mol_type = other DNA
                        organism = synthetic construct
                        note = Description of Artificial Sequence: Synthetic primer
SEQUENCE: 21
ccttcctggc tgtaggatct c                                                 21

SEQ ID NO: 22           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 22
cagatatgga aggtgcactg                                                   20

SEQ ID NO: 23           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 23
attccaaatg gctgcaaact                                                   20

SEQ ID NO: 24           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 24
agctgttgcc gatgactttt                                                   20

SEQ ID NO: 25           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 25
agcttgctca gcttgtactc                                                   20

SEQ ID NO: 26           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 26
cggcggtaca ctgcaggtgg                                                   20

SEQ ID NO: 27           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 27
gcaacatggc ctgcctgagt                                                   20

SEQ ID NO: 28           moltype = DNA   length = 20
FEATURE                 Location/Qualifiers
source                  1..20
                        mol_type = other DNA
                        organism = synthetic construct
                        note = Description of Artificial Sequence: Synthetic primer
SEQUENCE: 28
tttttgtctc ctgcctgagt                                                   20

SEQ ID NO: 29           moltype = AA    length = 660
FEATURE                 Location/Qualifiers
source                  1..660
                        mol_type = protein
                        organism = synthetic construct
```

```
                    note = Description of Artificial Sequence: Synthetic
                        polypeptide
SEQUENCE: 29
MDGFAGSLDD  SISAASTSDV  QDRLSALESR  VQQQEDEITV  LKAALADVLR  RLAISEDHVA   60
SVKKSVSSKG  QPSPRAVIPM  SCITNGSGAN  RKPSHTSAVS  IAGKETLSSA  AKSGTEKKKE  120
KPQGQREKKE  ESHSNDQSPQ  IRASPSPQPS  SQPLQIHRQT  PESKNATPTK  SIKRPSPAEK  180
SHNSWENSDD  SRNKLSKIPS  TPKLIPKVTK  TADKHKDVII  NQEGEYIKMF  MRGRPITMFI  240
PSDVDNYDDI  RTELPPEKLK  LEWAYGYRGK  DCRANVYLLP  TGEIVYFIAS  VVVLFNYEER  300
TQRHYLGHTD  CVKCLAIHPD  KIRIATGQIA  GVDKDGRPLQ  PHVRVWDSVT  LSTLQIIGLG  360
TFERGVGCLD  FSKADSGVHL  CVIDDSNEHM  LTVWDWQKKA  KGAEIKTTNE  VVLAVEFHPT  420
DANTIITCGK  SHIFFWTWSG  NSLTRKQGIF  GKYEKPKFVQ  CLAFLGNGDV  LTGDSGGVML  480
IWSKTTVEPT  PGKGPKGVYQ  ISKQIKAHDG  SVFTLCQMRN  GMLLTGGGKD  RKIILWDHDL  540
NPEREIEVPD  QYGTIRAVAE  GKADQFLVGT  SRNFILRGTF  NDGFQIEVQG  HTDELWGLAT  600
HPFKDLLLTC  AQDRQVCLWN  SMEHRLEWTR  LVDEPGHCAD  FHPSGTVVAI  GTHSGRPCCS  660

SEQ ID NO: 30           moltype = AA   length = 1250
FEATURE                 Location/Qualifiers
source                  1..1250
                        mol_type = protein
                        organism = synthetic construct
                        note = Description of Artificial Sequence: Synthetic
                            polypeptide
SEQUENCE: 30
MDGFAGSLDD  SISAASTSDV  QDRLSALESR  VQQQEDEITV  LKAALADVLR  RLAISEDHVA   60
SVKKSVSSKG  QPSPRAVIPM  SCITNGSGAN  RKPSHTSAVS  IAGKETLSSA  AKSGTEKKKE  120
KPQGQREKKE  ESHSNDQSPQ  IRASPSPQPS  SQPLQIHRQT  PESKNATPTK  SIKRPSPAEK  180
SHNSWENSDD  SRNKLSKIPS  TPKLIPKVTK  TADKHKDVII  NQEGEYIKMF  MRGRPITMFI  240
PSDVDNYDDI  RTELPPEKLK  LEWAYGYRGK  DCRANVYLLP  TGEIVYFIAS  VVVLFNYEER  300
TQRHYLGHTD  CVKCLAIHPD  KIRIATGQIA  GVDKDGRPLQ  PHVRVWDSVT  LSTLQIIGLG  360
TFERGVGCLD  FSKADSGVHL  CVIDDSNEHM  LTVWDWQKKA  KGAEIKTTNE  VVLAVEFHPT  420
DANTIITCGK  SHIFFWTWSG  NSLTRKQGIF  GKYEKPKFVQ  CLAFLGNGDV  LTGDSGGVML  480
IWSKTTVEPT  PGKGPKGVYQ  ISKQIKAHDG  SVFTLCQMRN  GMLLTGGGKD  RKIILWDHDL  540
NPEREIEVPD  QYGTIRAVAE  GKADQFLVGT  SRNFILRGTF  NDGFQIEVQG  HTDELWGLAT  600
HPFKDLLLTC  AQDRQVCLWN  SMEHRLEWTR  LVDEPGHCAD  FHPSGTVVAI  GTHSGRRQKH  660
EVNFPKIKLI  KKCGMLPGHV  AADHPPAVYR  RKHQELQAMQ  MELQSPEYKL  SKLRTSTIMT  720
DYNPNYCFAG  KTSSISDLKE  VPRKNITLIR  GLGHGAFGEV  YEGQVSGMPN  DPSPLQVAVK  780
TLPEVCSEQD  ELDFLMEALI  ISKFNHQNIV  RCIGVSLQSL  PRFILLELMA  GGDLKSFLRE  840
TRPRPSQPSS  LAMLDLLHVA  RDIACGCQYL  EENHFIHRDI  AARNCLLTCP  GPGRVAKIGD  900
FGMARDIYRA  SYYRKGGCAM  LPVKWMPPEA  FMEGIFTSKT  DTWSFGVLLW  EIFSLGYMPY  960
PSKSNQEVLE  FVTSGGRMDP  PKNCPGPVYR  IMTQCWQHQP  EDRPNFAIIL  ERIEYCTQDP 1020
DVINTALPIE  YGPLVEEEEK  VPVRPKDPEG  VPPLLVSQQA  KREEERSPAA  PPPLPTTSSG 1080
KAAKKPTAAE  ISVRVPRGPA  VEGGHVNMAF  SQSNPPSELH  KVHGSRNKPT  SLWNPTYGSW 1140
FTEKPTKKNN  PIAKKEPHDR  GNLGLEGSCT  VPPNVATGRL  PGASLLLEPS  SLTANMKEVP 1200
LFRLRHFPCG  NVNYGYQQQG  LPLEAATAPG  AGHYEDTILK  SKNSMNQPGP            1250

SEQ ID NO: 31           moltype = DNA   length = 150
FEATURE                 Location/Qualifiers
source                  1..150
                        mol_type = other DNA
                        organism = synthetic construct
                        note = Description of Artificial Sequence: Synthetic
                            polynucleotide
SEQUENCE: 31
gctcctggtg cttccggcgg tacactgcag gtgggtggtc agctgcaaca tggcctggca   60
gcattccaca tttttaatg agtttaattt tgggaaaatt gacttcatgt ttttgtctcc  120
tgcctgagtg cgttcctatg gccaccactg                                   150

SEQ ID NO: 32           moltype = DNA   length = 78
FEATURE                 Location/Qualifiers
source                  1..78
                        mol_type = other DNA
                        organism = synthetic construct
SEQUENCE: 32
gctcctggtg cttccggcgg tacactgcag gtgggtggtc agctgcaaca tggcctggca   60
gcattccaca tttttaa                                                  78

SEQ ID NO: 33           moltype = DNA   length = 72
FEATURE                 Location/Qualifiers
source                  1..72
                        mol_type = other DNA
                        organism = synthetic construct
SEQUENCE: 33
tgagttttaat tttgggaaaa ttgacttcat gttttgtct cctgcctgag tgcgttccta   60
tggccaccac tg                                                       72
```